United States Patent
Carling et al.

(10) Patent No.: US 7,015,224 B2
(45) Date of Patent: Mar. 21, 2006

(54) 7-TERT-BUTYL-3-(2-FLUOROPHENYL)-6-(2H-(1,2,4)TRIAZOL-3-YLMETHOXY)-(1,2,4) TRIAZOLO (4,3B) PYRIDAZINE FOR THE TREATMENT OF ANXIETY AND CONVULSIONS

(75) Inventors: Robert William Carling, Bishops Stortford (GB); Kevin William Moore, Buntingford (GB); Leslie Joseph Street, Little Hallingbury (GB)

(73) Assignee: Merck Sharp & Dohme Ltd., Hoddesdon ( * ) Notice: Subject to any disclaimer, the term of this patent is extended or adjusted under 35 U.S.C. 154(b) by 147 days.

(21) Appl. No.: 10/490,077

(22) PCT Filed: Sep. 13, 2002

(86) PCT No.: PCT/GB02/04201

§ 371 (c)(1),
(2), (4) Date: Mar. 18, 2004

(87) PCT Pub. No.: WO03/024968

PCT Pub. Date: Mar. 27, 2003

(65) Prior Publication Data

US 2004/0242586 A1    Dec. 2, 2004

(30) Foreign Application Priority Data

Sep. 20, 2001  (GB) .................... 0122696

(51) Int. Cl.
A61K 37/5025    (2006.01)
C07D 487/02     (2006.01)
C07D 237/26     (2006.01)
(52) U.S. Cl. ..................... 514/248; 544/235
(58) Field of Classification Search ................ 544/236
See application file for complete search history.

(56) References Cited

FOREIGN PATENT DOCUMENTS

WO    WO 98 04559 A    2/1998
WO    WO 00/47582 A1 *  8/2000

* cited by examiner

*Primary Examiner*—Kamal A. Saeed
*Assistant Examiner*—Jason M. Nolan
(74) *Attorney, Agent, or Firm*—J. Eric Thies; Melvin Winokur

(57) ABSTRACT

The compound (I) is a $GABA_a$ receptor ligand, functionally selective for the α2 and/or α3 subunit, and is useful in the treatment of deleterious mental states, in particular anxiety.

6 Claims, No Drawings

7-TERT-BUTYL-3-(2-FLUOROPHENYL)-6-(2H-(1,2,4)TRIAZOL-3-YLMETHOXY)-(1,2,4) TRIAZOLO (4,3B) PYRIDAZINE FOR THE TREATMENT OF ANXIETY AND CONVULSIONS

CROSS REFERENCE TO RELATED APPLICATIONS

This application is a U.S. National Phase application under 35 U.S.C. §371 of PCT Application No. PCT/GB02/04201, filed Sep. 13, 2002, which claims priority under 35 U.S.C. §119 from GB Application No. 0122696.8, filed Sep. 20, 2001.

The present invention relates to a substituted triazolopyridazine derivative and to its use in therapy. More particularly, this invention is concerned with a particular substituted [1,2,4]triazolo[4,3-b]pyridazine derivative which is a $GABA_A$ receptor ligand and is therefore useful in the therapy of deleterious mental states.

Receptors for the major inhibitory neurotransmitter, gamma-aminobutyric acid (GABA), are divided into two main classes: (1) $GABA_A$ receptors, which are members of the ligand-gated ion channel superfamily; and (2) $GABA_B$ receptors, which may be members of the G-protein linked receptor superfamily. Since the first cDNAs encoding individual $GABA_A$ receptor subunits were cloned the number of known members of the mammalian family has grown to include at least six $\alpha$ subunits, four $\beta$ subunits, three $\gamma$ subunits, one $\delta$ subunit, one $\epsilon$ subunit and two $\rho$ subunits.

Although knowledge of the diversity of the $GABA_A$ receptor gene family represents a huge step forward in our understanding of this ligand-gated ion channel, insight into the extent of subtype diversity is still at an early stage. It has been indicated that an $\alpha$ subunit, a $\beta$ subunit and a $\gamma$ subunit constitute the minimum requirement for forming a fully functional $GABA_A$ receptor expressed by transiently transfecting cDNAs into cells. As indicated above, $\delta$, $\epsilon$ and $\rho$ subunits also exist, but are present only to a minor extent in $GABA_A$ receptor populations.

Studies of receptor size and visualisation by electron microscopy conclude that, like other members of the ligand-gated ion channel family, the native $GABA_A$ receptor exists in pentameric form. The selection of at least one $\alpha$, one $\beta$ and one $\gamma$ subunit from a repertoire of seventeen allows for the possible existence of more than 10,000 pentameric subunit combinations. Moreover, this calculation overlooks the additional permutations that would be possible if the arrangement of subunits around the ion channel had no constraints (i.e. there could be 120 possible variants for a receptor composed of five different subunits).

Receptor subtype assemblies which do exist include, amongst many others, $\alpha 1\beta 2\gamma 2$, $\alpha 2\beta 2/3\gamma 2$, $\alpha 3\beta\gamma 2/3$, $\alpha 2\beta\gamma 1$, $\alpha 5\beta 3\gamma 2/3$, $\alpha 6\beta\gamma 2$, $\alpha 6\beta\delta$ and $\alpha 4\beta\delta$. Subtype assemblies containing an $\alpha 1$ subunit are present in most areas of the brain and are thought to account for over 40% of $GABA_A$ receptors in the rat. Subtype assemblies containing $\alpha 2$ and $\alpha 3$ subunits respectively are thought to account for about 25% and 17% of $GABA_A$ receptors in the rat. Subtype assemblies containing an $\alpha 5$ subunit are expressed predominantly in the hippocampus and cortex and are thought to represent about 4% of $GABA_A$ receptors in the rat.

A characteristic property of all known $GABA_A$ receptors is the presence of a number of modulatory sites, one of which is the benzodiazepine (BZ) binding site. The BZ binding site is the most explored of the $GABA_A$ receptor modulatory sites, and is the site through which anxiolytic drugs such as diazepam and temazepam exert their effect. Before the cloning of the $GABA_A$ receptor gene family, the benzodiazepine binding site was historically subdivided into two subtypes, BZ1 and BZ2, on the basis of radioligand binding studies. The BZ1 subtype has been shown to be pharmacologically equivalent to a $GABA_A$ receptor comprising the $\alpha 1$ subunit in combination with a $\beta$ subunit and $\gamma 2$. This is the most abundant $GABA_A$ receptor subtype, and is believed to represent almost half of all $GABA_A$ receptors in the brain.

Two other major populations are the $\alpha 2\beta\gamma 2$ and $\alpha 3\beta\gamma 2/3$ subtypes. Together these constitute approximately a further 35% of the total $GABA_A$ receptor repertoire. Pharmacologically this combination appears to be equivalent to the BZ2 subtype as defined previously by radioligand binding, although the BZ2 subtype may also include certain $\alpha 5$-containing subtype assemblies. The physiological role of these subtypes has hitherto been unclear because no sufficiently selective agonists or antagonists were known.

It is now believed that agents acting as BZ agonists at $\alpha 1\beta\gamma 2$, $\alpha 2\beta\gamma 2$ or $\alpha 3\beta\gamma 2$ subtypes will possess desirable anxiolytic properties. Compounds which are modulators of the benzodiazepine binding site of the $GABA_A$ receptor by acting as BZ agonists are referred to hereinafter as "$GABA_A$ receptor agonists". The $\alpha 1$-selective $GABA_A$ receptor agonists alpidem and zolpidem are clinically prescribed as hypnotic agents, suggesting that at least some of the sedation associated with known anxiolytic drugs which act at the BZ1 binding site is mediated through $GABA_A$ receptors containing the $\alpha 1$ subunit. Accordingly, it is considered that $GABA_A$ receptor agonists which interact more favourably with the $\alpha 2$ and/or $\alpha 3$ subunit than with $\alpha 1$ will be effective in the treatment of anxiety with a reduced propensity to cause sedation. Also, agents which are antagonists or inverse agonists at $\alpha 1$ might be employed to reverse sedation or hypnosis caused by $\alpha 1$ agonists.

The compounds of the present invention, being selective ligands for $GABA_A$ receptors, are therefore of use in the treatment and/or prevention of a variety of disorders of the central nervous system. Such disorders include anxiety disorders, such as panic disorder with or without agoraphobia, agoraphobia without history of panic disorder, animal and other phobias including social phobias, obsessive-compulsive disorder, stress disorders including post-traumatic and acute stress disorder, and generalized or substance-induced anxiety disorder; neuroses; convulsions; migraine; depressive or bipolar disorders, for example single-episode or recurrent major depressive disorder, dysthymic disorder, bipolar I and bipolar II manic disorders, and cyclothymic disorder; psychotic disorders including schizophrenia; neurodegeneration arising from cerebral ischemia; attention deficit hyperactivity disorder; speech disorders, including stuttering; and disorders of circadian rhythm, e.g. in subjects suffering from the effects of jet lag or shift work.

Further disorders for which selective ligands for GABA$_A$ receptors may be of benefit include pain and nociception; emesis, including acute, delayed and anticipatory emesis, in particular emesis induced by chemotherapy or radiation, as well as motion sickness, and post-operative nausea and vomiting; eating disorders including anorexia nervosa and bulimia nervosa; premenstrual syndrome; muscle spasm or spasticity, e.g. in paraplegic patients; hearing disorders, including tinnitus and age-related hearing impairment; urinary incontinence; and the effects of substance abuse and dependency, including alcohol withdrawal. Selective ligands for GABA$_A$ receptors may also be effective as pre-medication prior to anaesthesia or minor procedures such as endoscopy, including gastric endoscopy.

In addition, the compounds in accordance with the present invention may be useful as radioligands in assays for detecting compounds capable of binding to the human GABA$_A$ receptor.

WO 98/04559 describes a class of substituted and 7,8-ring fused [1,2,4]triazolo[4,3-b]pyridazine derivatives which are stated to be selective ligands for GABA$_A$ receptors beneficial in the treatment and/or prevention of neurological disorders including anxiety and convulsions.

The present invention provides a particular triazolo-pyridazine derivative, and pharmaceutically acceptable salts thereof, which possess desirable binding properties at various GABA$_A$ receptor subtypes. The compounds in accordance with the present invention have good affinity as ligands for the α2 and/or α3 subunit of the human GABA$_A$ receptor. The compounds of this invention interact more favourably with the α2 and/or α3 subunit than with the α1 subunit. Indeed, the compounds of the invention exhibit functional selectivity in terms of a selective efficacy for the α2 and/or α3 subunit relative to the α1 subunit.

The compounds of the present invention are GABA$_A$ receptor subtype ligands having a binding affinity (K$_i$) for the α2 and/or α3 subunit, as measured in the assay described hereinbelow, of less than 1 nM. Furthermore, the compounds in accordance with this invention exhibit functional selectivity in terms of a selective efficacy for the α2 and/or α3 subunit relative to the α1 subunit. Moreover, the compounds according to the present invention possess interesting pharmacokinetic properties, notably in terms of improved oral bioavailability.

The present invention provides 7-tert-butyl-3-(2-fluorophenyl)-6-(2H-[1,2,4]triazol-3-ylmethoxy)-[1,2,4]triazolo[4,3-b]pyridazine of formula I:

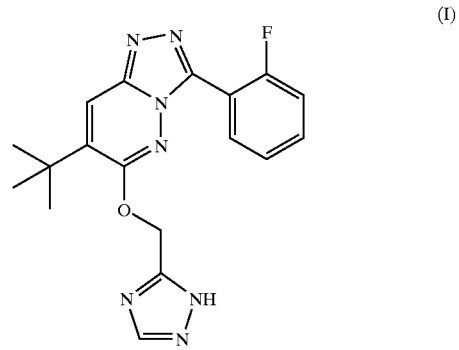

or a pharmaceutically acceptable salt thereof.

The present invention also provides 7-tert-butyl-3-(2-fluorophenyl)-6-(2H-[1,2,4]triazol-3-ylmethoxy)-[1,2,4]triazolo[4,3-b]pyridazine of formula I as depicted above, or a pharmaceutically acceptable salt thereof, in isolated form.

The compounds in accordance with the present invention are encompassed within the generic scope of WO 98/04559. There is, however, no specific disclosure therein of the compound of formula I as depicted above, or pharmaceutically acceptable salts thereof.

For use in medicine, the salts of the compound of formula I above will be pharmaceutically acceptable salts. Other salts may, however, be useful in the preparation of the compound of formula I or of its pharmaceutically acceptable salts. Suitable pharmaceutically acceptable salts of the compound of formula I include acid addition salts which may, for example, be formed by mixing a solution of the compound of formula I with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

Also provided by the present invention is a method for the treatment and/or prevention of anxiety which comprises administering to a patient in need of such treatment an effective amount of the compound of formula I as depicted above or a pharmaceutically acceptable salt thereof.

Further provided by the present invention is a method for the treatment and/or prevention of convulsions (e.g. in a patient suffering from epilepsy or a related disorder) which comprises administering to a patient in need of such treatment an effective amount of the compound of formula I as depicted above or a pharmaceutically acceptable salt thereof.

The binding affinity (K$_i$) of the compounds according to the present invention for the α3 subunit of the human GABA$_A$ receptor is conveniently as measured in the assay described hereinbelow. The α3 subunit binding affinity (K$_i$) of the compounds of the invention is less than 1 nM.

The compounds according to the present invention elicit a selective potentiation of the GABA EC$_{20}$ response in stably transfected recombinant cell lines expressing the α3 subunit of the human $GABA_A$ receptor relative to the potentiation of the GABA $EC_{20}$ response elicited in stably transfected recombinant cell lines expressing the α1 subunit of the human $GABA_A$ receptor.

The potentiation of the GABA $EC_{20}$ response in stably transfected cell lines expressing the α3 and α1 subunits of the human $GABA_A$ receptor can conveniently be measured by procedures analogous to the protocol described in Wafford et al., *Mol. Pharmacol.*, 1996, 50, 670–678. The procedure will suitably be carried out utilising cultures of stably transfected eukaryotic cells, typically of stably transfected mouse Ltk⁻ fibroblast cells.

The compounds according to the present invention exhibit anxiolytic activity, as demonstrated by a positive response in the elevated plus maze and conditioned suppression of drinking tests (cf. Dawson et al., *Psychopharmacology*, 1995, 121, 109–117). Moreover, the compounds of the invention are substantially non-sedating, as confirmed by an appropriate result obtained from the response sensitivity (chain-pulling) test (cf. Bayley et al., *J. Psychopharmacol.*, 1996, 10, 206–213).

The compounds according to the present invention may also exhibit anticonvulsant activity. This can be demonstrated by the ability to block pentylenetetrazole-induced seizures in rats and mice, following a protocol analogous to that described by Bristow et al. in *J. Pharmacol. Exp. Ther.*, 1996, 279, 492–501.

Advantageously, the compounds of the invention will be capable of exerting their beneficial therapeutic action following administration by the oral route.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action.

For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of anxiety, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compound of formula I as depicted above may be prepared by a process which comprises reacting a compound of formula III with a compound of formula IV:

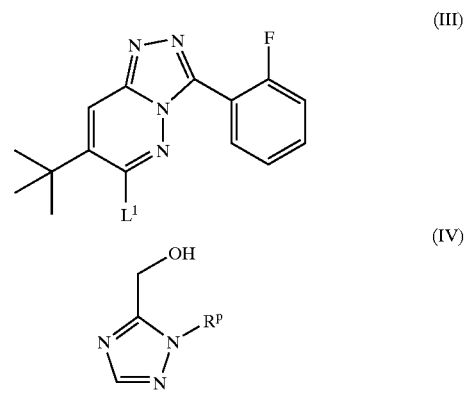

wherein $L^1$ represents a suitable leaving group, and $R^P$ represents an amino-protecting group; followed by removal of the amino-protecting group $R^P$.

The leaving group $L^1$ is typically a halogen atom, especially chloro.

The amino-protecting group $R^P$ suitably comprises 2-(trimethylsilanyl)ethoxymethyl, in which case removal of the amino-protecting group $R^P$ can be conveniently effected by treatment with a mineral acid such as hydrochloric acid in a lower alkanol such as ethanol.

The reaction between compounds III and IV is conveniently effected by stirring the reactants in a suitable solvent, in the presence of a base. Typically, the solvent is N,N-dimethylformamide, and the base is a strong base such as lithium hexamethyldisilazide.

In another procedure, the compound of formula I as depicted above may be prepared by a process which comprises reacting the compound of formula V (or its [1,2,4] triazolo[4,3-b]pyridazin-6-one tautomer) with a compound of formula VII:

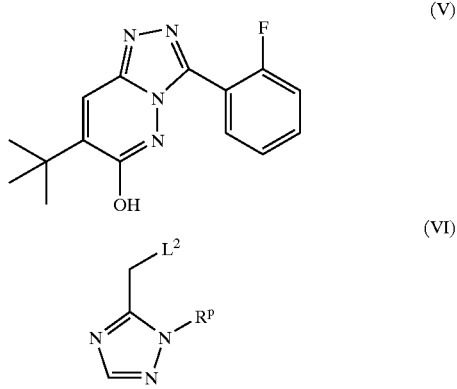

(V)

(VI)

wherein $R^P$ is as defined above, and $L^2$ represents a suitable leaving group; followed by removal of the amino-protecting group $R^P$.

The leaving group $L^2$ is suitably a halogen atom, typically chloro or bromo.

The reaction between compounds V and VI is conveniently effected by stirring the reactants in a suitable solvent, typically N,N-dimethylformamide, in the presence of a strong base such as sodium hydride.

The intermediate of formula V above may conveniently be prepared by reacting a compound of formula III as defined above with an alkali metal hydroxide, e.g. sodium hydroxide. The reaction is conveniently effected in an inert solvent such as aqueous 1,4-dioxane, ideally at the reflux temperature of the solvent.

In a further procedure, the compound of formula I as depicted above may be prepared by a process which comprises reacting trimethylacetic acid with a compound of formula VII:

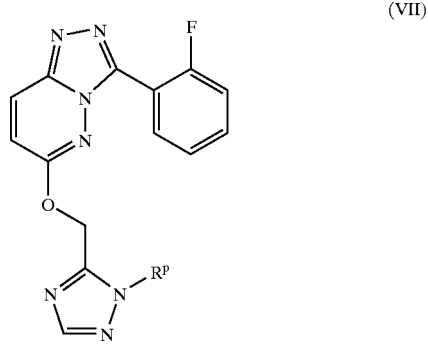

(VII)

wherein $R^P$ is as defined above; in the presence of silver nitrate and ammonium persulphate; followed by removal of the amino-protecting group $R^P$.

The reaction is conveniently carried out in a suitable solvent, for example in water or aqueous acetonitrile, optionally under acidic conditions, e.g. using trifluoroacetic acid or sulphuric acid, typically at an elevated temperature.

In a still further procedure, the compound of formula I as depicted above may be prepared by a process which comprises reacting a compound of formula VIII with a compound of formula IX:

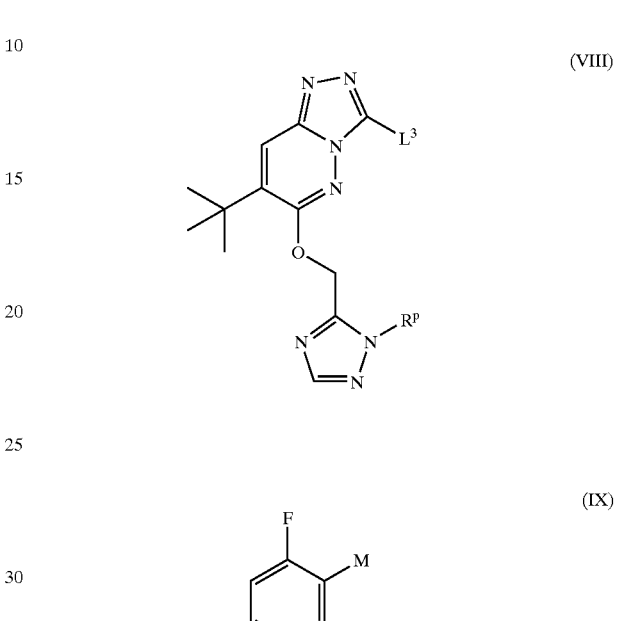

(VIII)

(IX)

wherein $R^P$ is as defined above, M represents —B(OH)$_2$ or —Sn(Alk)$_3$ in which Alk represents a $C_{1-6}$ alkyl group, typically n-butyl, and $L^3$ represents a suitable leaving group; in the presence of a transition metal catalyst; followed by removal of the amino-protecting group $R^P$.

The leaving group $L^3$ is suitably a halogen atom, e.g. bromo.

A suitable transition metal catalyst of use in the reaction between compounds VIII and IX comprises dichlorobis (triphenylphosphine)-palladium(II) or tetrakis(triphenylphosphine)palladium(O).

The reaction between compounds VIII and IX is conveniently effected in an inert solvent such as N,N-dimethylformamide, typically at an elevated temperature.

The intermediates of formula VIII may be prepared by reacting a compound of formula IV as defined above with a compound of formula X:

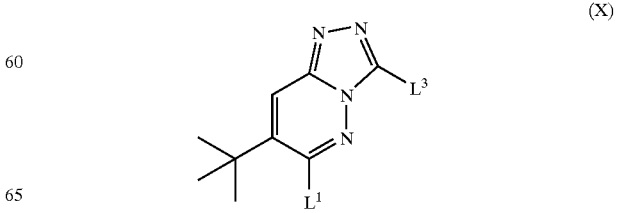

(X)

wherein $L^1$ and $L^3$ are as defined above; under conditions analogous to those described above for the reaction between compounds III and IV.

The intermediates of formula III above may be prepared by the procedures described in WO 98/04559 and WO 00/47582, or by methods analogous thereto.

Typical intermediates of formula IV, VI, VII and X above may be prepared as described in WO 98/04559, or by methods analogous thereto.

Where they are not commercially available, the starting materials of formula IX may be prepared by standard methods well known from the art.

The following Examples illustrate the preparation of compounds according to the invention.

The compounds in accordance with this invention potently inhibit the binding of [$^3$H]-flumazenil to the benzodiazepine binding site of human GABA$_A$ receptors containing the α2 or α3 subunit stably expressed in Ltk$^-$ cells.

Reagents

Phosphate buffered saline (PBS).

Assay buffer: 10 mM KH$_2$PO$_4$, 100 mM KCl, pH 7.4 at room temperature.

[$^3$H]-Flumazenil (18 nM for α1β3β2 cells; 18 nM for α2β3γ2 cells; 10 nM for α3β3γ2 cells) in assay buffer.

Flunitrazepam 100 μM in assay buffer.

Cells resuspended in assay buffer (1 tray to 10 ml).

Harvesting Cells

Supernatant is removed from cells. PBS (approximately 20 ml) is added. The cells are scraped and placed in a 50 ml centrifuge tube. The procedure is repeated with a further 10 ml of PBS to ensure that most of the cells are removed. The cells are pelleted by centrifuging for 20 min at 3000 rpm in a benchtop centrifuge, and then frozen if desired. The pellets are resuspended in 10 ml of buffer per tray (25 cm×25 cm) of cells.

Assay

Can be carried out in deep 96-well plates or in tubes. Each tube contains:

300 μl of assay buffer.

50 μl of [$^3$H]-flumazenil (final concentration for α1β3γ2: 1.8 nM; for α2β3γ2: 1.8 nM; for α3β3γ2: 1.0 nM).

50 μl of buffer or solvent carrier (e.g. 10% DMSO) if compounds are dissolved in 10% DMSO (total); test compound or flunitrazepam (to determine non-specific binding), 10 μM final concentration.

100 μl of cells.

Assays are incubated for 1 hour at 40° C., then filtered using either a Tomtec or Brandel cell harvester onto GF/B filters followed by 3×3 ml washes with ice cold assay buffer. Filters are dried and counted by liquid scintillation counting. Expected values for total binding are 3000–4000 dpm for total counts and less than 200 dpm for non-specific binding if using liquid scintillation counting, or 1500–2000 dpm for total counts and less than 200 dpm for non-specific binding if counting with meltilex solid scintillant. Binding parameters are determined by non-linear least squares regression analysis, from which the inhibition constant $K_i$ can be calculated for each test compound.

The compound of the accompanying Examples was tested in the above assay, and was found to possess a $K_i$ value for displacement of [$^3$H]-flumazenil from the α2 and/or α3 subunit of the human GABA$_A$ receptor of less than 1 nM.

EXAMPLE 1

7-tert-Butyl-3-(2-fluorophenyl-6-(2H-[1,2,4]triazol-3-ylmethoxy)-[1,2,4]triazolo[4,3-b]pyridazine a) 7-tert-Butyl-3-(2-fluorophenyl)-6-[2-(2-(trimethylsilanyl)ethoxymethyl)-2H-[1 2,4]triazol-3-ylmethoxy]-[1,2,4]triazolo[4,3-b]pyridazine To a solution of [2-(2-(trimethylsilanyl)ethoxymethyl)-2H-[1,2,4]triazol-3-yl]methanol (180 mg, 0.79 mM, WO 98/04559) and 7-tert-butyl-6-chloro-3-(2-fluorophenyl)-[1,2,4]triazolo[4,3-b]pyridazine (200 mg, 0.66 mM, WO 00/47582) in N,N-dimethylformamide (15 ml) was added a solution of lithium hexamethyldisilazide (0.72 ml of a 1 mM solution in tetrahydrofuran) and the reaction mixture was stirred for 1 h. Water was added until the solution became cloudy and after 30 min a solid was collected by filtration. The solid was washed with water, dissolved in dichloromethane and dried (MgSO$_4$), filtered and evaporated to give the desired product (250 mg). $^1$H NMR (360 MHz, CDCl$_3$) δ 0.01 (9H, s), 0.86 (2H, t, J 7.3 Hz), 1.47 (9H, s), 3.57 (2H, t, J 7.3 Hz), 5.43 (2H, s), 5.61 (2H, s), 7.29–7.41 (2H, m), 7.61 (1H, m), 7.86 (1H, t, J 1.8 Hz), 7.96 (1H, s), 8.02 (1H, s); MS (ES$^+$) m/e 498 [MH]$^+$. Anal. Found C, 57.80; H, 6.49; N, 19.49. C$_{24}$H$_{32}$FN$_7$O$_2$Si requires C, 57.92; H, 6.48; N, 19.70%.

b) 7-tert-Butyl-3-(2-fluorophenol)-6-(2H-[1,2,4]triazol-3-ylmethoxy)-[1,2,4]triazolo[4,3-b]pyridazine To a solution of 7-tert-butyl-3-(2-fluorophenyl)-6-[2-(2-(trimethylsilanyl)ethoxymethyl)-2H-[1,2,4]triazol-3-yl-methoxy]-[1,2,4]triazolo[4,3-b]pyridazine (200 mg, 0.40 mM) in ethanol (5 ml) was added hydrochloric acid (1 ml of 2 mM) and the reaction mixture was heated to 60° C. for 5 h. After cooling solid potassium carbonate was added slowly until the solution was pH 10. The solution was allowed to stand for 18 h and the product was collected by filtration. The product was washed with water and recrystallized from a mixture of dichloromethane and ethyl acetate to give the desired product (82 mg). $^1$H NMR (360 MHz, DMSO) δ 1.39 (9H, s), 5.42 (2H, s), 7.41–7.50 (2H, m), 7.63–7.67 (1H, m), 7.98 (1H, m), 8.10 (1H, s), 8.60 (1H, s), 14.05 (1H, bs); MS (ES+) m/e 368 [MH]$^+$. Anal. Found C, 57.74; H, 4.97; N, 26.03. C$_{18}$H$_{18}$FN$_7$O.0.5 H$_2$O requires C, 57.44; H, 5.09; N, 26.05%.

The invention claimed is:

1. A compound 7-tert-butyl-3-(2-fluorophenyl)-6-(2H-[1,2,4]triazol-3-ylmethoxy)-[1,2,4]triazolo[4,3-b]pyridazine of the formula I:

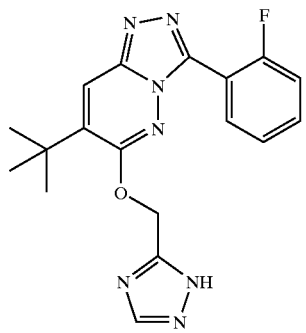

or a pharmaceutically acceptable salt thereof.

2. A compound 7-tert-butyl-3-(2-fluorophenyl)-6-(2H-[1,2,4]triazol-3-ylmethoxy)-[1,2,4]triazolo[4,3-b]pyridazine of the formula I:

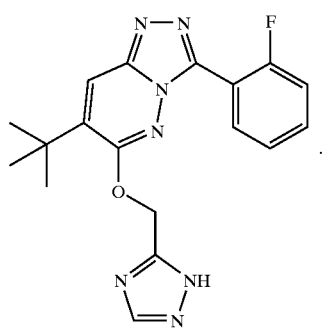

3. A pharmaceutical composition comprising the compound of claim 1 or a pharmaceutically acceptable salt thereof and a pharmaceutically acceptable carrier.

4. A method for the treatment of anxiety which comprises administering to a patient in need of such treatment an effective amount of the compound of claim 1 or a pharmaceutically acceptable salt thereof.

5. A method for the treatment of convulsions which comprises administering to a patient in need of such treatment an effective amount of the compound of claim 1 or a pharmaceutically acceptable salt thereof.

6. A process for the preparation of the compound of claim 1 which comprises reacting a compound of formula III with a compound of formula IV:

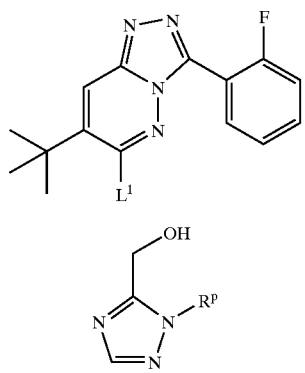

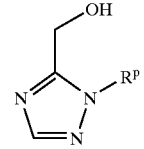

wherein $L^1$ represents a suitable leaving group, and $R^P$ represents an amino-protecting group; followed by removal of the amino-protecting group $R^P$.

* * * * *